United States Patent
Lu et al.

(10) Patent No.: US 12,138,479 B2
(45) Date of Patent: Nov. 12, 2024

(54) INDEPENDENT STEREOTACTIC RADIOTHERAPY DOSE CALCULATION AND TREATMENT PLAN VERIFICATION

(71) Applicant: THE BOARD OF REGENTS OF THE UNIVERSITY OF TEXAS SYSTEM, Austin, TX (US)

(72) Inventors: Weiguo Lu, Coppell, TX (US); Xuejun Gu, Dallas, TX (US); Mingli Chen, Coppell, TX (US); Xun Jia, Dallas, TX (US); Steve Bin Jiang, Southlake, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 380 days.

(21) Appl. No.: 17/597,509

(22) PCT Filed: Jul. 13, 2020

(86) PCT No.: PCT/US2020/041848
§ 371 (c)(1),
(2) Date: Jan. 10, 2022

(87) PCT Pub. No.: WO2021/011499
PCT Pub. Date: Jan. 21, 2021

(65) Prior Publication Data
US 2022/0249867 A1 Aug. 11, 2022

Related U.S. Application Data

(60) Provisional application No. 62/873,501, filed on Jul. 12, 2019, provisional application No. 62/873,515, filed on Jul. 12, 2019.

(51) Int. Cl.
*A61N 5/10* (2006.01)

(52) U.S. Cl.
CPC ......... *A61N 5/1031* (2013.01); *A61N 5/1075* (2013.01); *A61N 5/1077* (2013.01);
(Continued)

(58) Field of Classification Search
None
See application file for complete search history.

(56) References Cited

U.S. PATENT DOCUMENTS

| 6,029,079 A | 2/2000 | Cox et al. |
| 2011/0022360 A1 | 1/2011 | Simon et al. |

(Continued)

OTHER PUBLICATIONS

International Application No. PCT/US2020/041848, International Preliminary Report on Patentability and Written Opinion of the International Searching Authority, dated Jan. 27, 2022, 6 pages.

(Continued)

*Primary Examiner* — Hoon K Song
(74) *Attorney, Agent, or Firm* — DLA Piper LLP US

(57) ABSTRACT

The present disclosure is directed towards a treatment planning system for use in a stereotactic radiotherapy system. In particular, the disclosed systems and methods may be used for generating a treatment plan and/or verifying an existing treatment plan. Moreover, the disclosed systems and methods may be suitable for use in a clinical setting. A method for verifying a treatment plan of a stereotactic radiotherapy device may include the steps of receiving a treatment plan, generating a second treatment plan by applying a modified monte-carlo method to regions of interest in the treatment plan, and identifying discrepancies between the received treatment plan and the generated second treatment plan.

17 Claims, 13 Drawing Sheets

(52) U.S. Cl.
CPC ................ *A61N 2005/1034* (2013.01); *A61N 2005/1087* (2013.01)

(56) References Cited

U.S. PATENT DOCUMENTS

| | | |
|---|---|---|
| 2013/0197878 A1 | 8/2013 | Fiege et al. |
| 2018/0318609 A1 | 11/2018 | Arican et al. |
| 2019/0046813 A1* | 2/2019 | Zhou .................. A61N 5/10 |
| 2019/0076673 A1 | 3/2019 | Lu et al. |

OTHER PUBLICATIONS

Extended European Search Report issued in EP Application No. 20840341, 9 pages, dated Jul. 7, 2023.

* cited by examiner

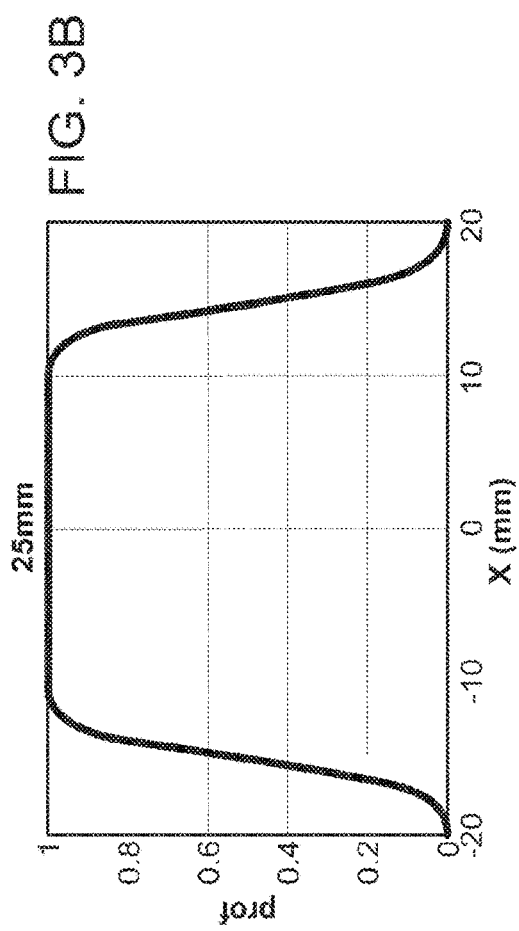
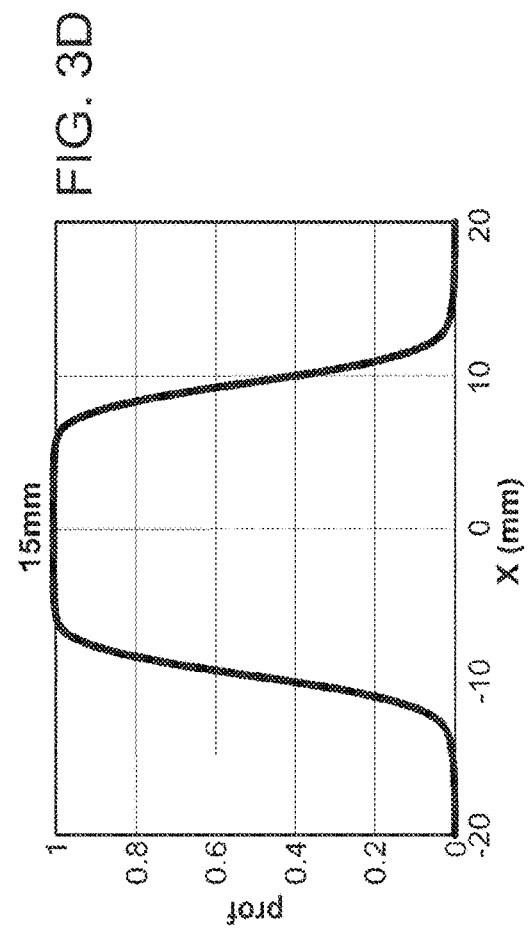
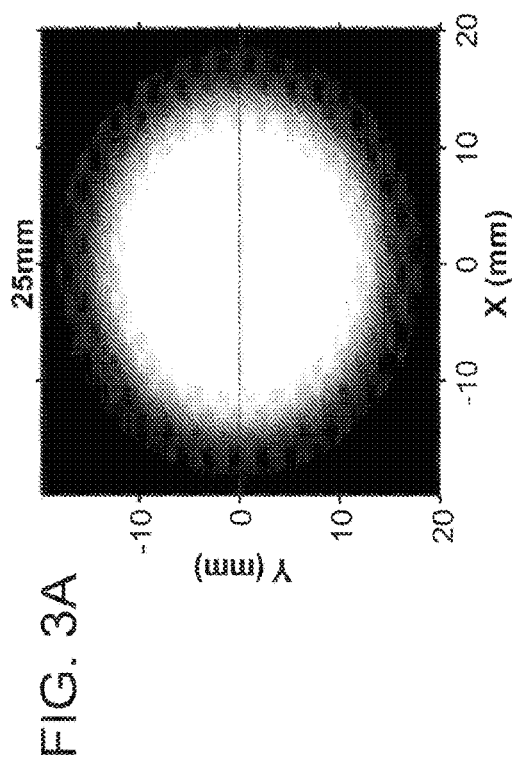
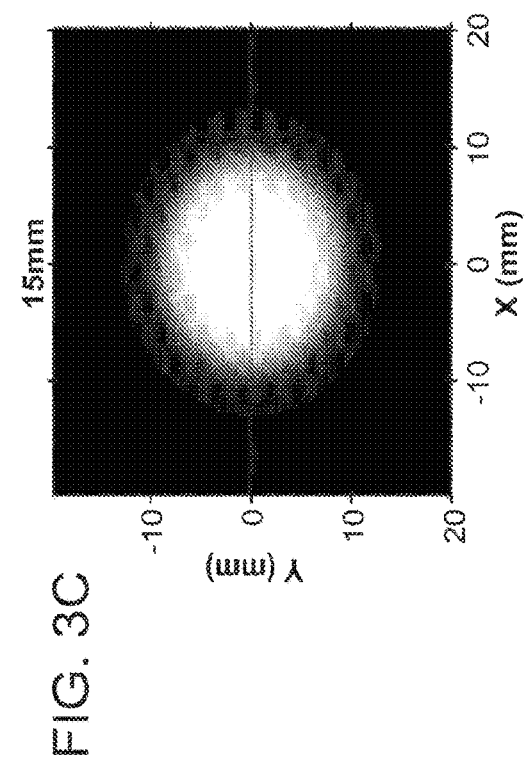
FIG. 3A
FIG. 3B
FIG. 3C
FIG. 3D

INDEPENDENT STEREOTACTIC RADIOTHERAPY DOSE CALCULATION AND TREATMENT PLAN VERIFICATION

CROSS-REFERENCE TO RELATED APPLICATIONS

This application is a 371 of International Application Number PCT/US2020/041848, filed Jul. 13, 2020, which claims priority from U.S. Provisional Application Ser. No. 62/873,515, filed Jul. 12, 2019, and U.S. Provisional Application Ser. No. 62/873,501, filed Jul. 12, 2019, which are hereby incorporated by reference in their entireties. The present disclosure is also related to the PCT application No. PCT/US2020/041842, filed Jul. 13, 2020, entitled "A Compact Dosimetric Data Collection Platform for a Breast Cancer Stereotactic Radiotherapy System," filed concurrently herewith and incorporated by reference in its entirety.

TECHNICAL FIELD

The present disclosure is directed to a stereotactic radiotherapy system.

BACKGROUND

A stereotactic radiotherapy system is configured to apply ionizing radiation to a targeted location, such as a cancerous tumor located in the breast tissue or brain.

Examples of a stereotactic radiotherapy system include a GammaPod™ and a GammaKnife™, as described in Yu et al, "Gammapod-A New Device Dedicated for Stereotactic Radiotherapy of Breast Cancer", Med Phys. 40(5) (May 2013), the contents of which is hereby incorporated by reference.

In stereotactic radiotherapy sessions one or more radiation sources may be distributed over a range of angles and used to apply a focused dose of radiation at a target area. A stereotactic radiotherapy system may be configured to include components that rotate continuously, creating thousands of beam angles that combine with one another to create an intense focal spot to apply radiotherapy. This method allows the surrounding healthy tissue to be spared. For example, in the GammaPod™ 25-36 radiation sources of Cobalt-60 are distributed over a range of latitudinal angles in a hemispherical structure to form multiple Gamma-ray beams aiming at the same isocenter or target location. The entire GammaPod™ structure is configured to rotate during treatment, creating multiple non-overlapping conical arcs to achieve highly focused dose distribution.

In conventional systems, a treatment planning system (TPS) for a stereotactic radiotherapy system is verified by a second dose calculation that is independently formed. A treatment plan may also need verification by an additional dose measurement when the second independent dose and TPS dose have large deviations. Treatment plan verification is very important since any dose deviation from the intended dose, such as underdose to the treatment target or overdose to the normal tissues, can cause adverse effects. However, conventional methods for generating a second dose calculation for verifying a treatment plan may require enormous amounts of time that may not be suitable for use in a clinical setting. Additionally, the unique mechanical design and treatment planning system (TPS) of the GammaPod™ system may pose additional challenges associated with system commissioning, the continued determination of quality assurance (QA) metrics, and continued generation of dose calculations.

SUMMARY

The present disclosure is directed towards a treatment planning system for use in a stereotactic radiotherapy system. In particular, the disclosed systems and methods may be used for generating a treatment plan and/or verifying an existing treatment plan. Moreover, the disclosed systems and methods may be suitable for use in a clinical setting.

In some embodiments, a method for verifying a treatment plan of a stereotactic radiotherapy device includes the steps of receiving a treatment plan, generating a second treatment plan by applying a modified monte-carlo method to regions of interest in the treatment plan, and identifying discrepancies between the received treatment plan and the generated second treatment plan.

In some embodiments, a system for providing a treatment plan for a stereotactic radiotherapy device includes a server system communicatively coupled to a backend server of the stereotactic radiotherapy device. The server system may be configured to: receive from the backend server of the stereotactic radiotherapy device at least one of imaging data of the target area and a treatment plan generated by the stereotactic radiotherapy device, apply a monte-carlo based dose generation module to generate a plurality of doses for locations among the target area, and generate a second treatment plan based on the generated plurality of doses.

In some embodiments, generating a second treatment plan includes generating a fluence map, generating a phase space map based on the generated fluence map, calculating a dose value for positions within the target area based on the phase space map, and compiling a second treatment plan based on the calculated dose values. The server system may be configured to generate a dose for locations among the target area within a time period of five minutes, and generate the second treatment plan within a time period of a week. Optionally, generating the fluence map may include calculating one or more parameters based on the physical geometry of the stereotactic radiotherapy device. The server system may also be configured to generate a quality assurance report. In some embodiments, at least a portion of the parameters for the monte-carlo based dose generation module may be pre-calculated. In some embodiments a compact beam scanner may be configured to obtain beam values and provide the obtained beam values to the dose generation module.

In some embodiments a method of providing a treatment plan for a stereotactic radiotherapy device includes the steps of receiving from the backend server of the stereotactic radiotherapy device at least one of imaging data of the target area and a treatment plan generated by the stereotactic radiotherapy device, applying a monte-carlo based dose generation module stored on a server system to generate a plurality of doses for locations among the target area, wherein the server system is communicatively coupled to the backend server of the stereotactic radiotherapy device, and generating a second treatment plan based on the generated plurality of doses.

Generating a treatment plan may include generating a fluence map, generating a phase space map based on the generated fluence map, calculating a dose value for positions within the target area based on the phase space map, and compiling a second treatment plan based on the calculated dose values. Optionally, at least a portion of the parameters for the monte-carlo based dose generation module may be pre-calculated. The method may also include the step of receiving data for the physical geometry of the stereotactic radiotherapy device from the backend server of the stereotactic radiotherapy device. Optionally, generating the phase space map may include using beam values obtained by a compact beam scanner. Generating the fluence map may include calculating one or more parameters based on the physical geometry of the stereotactic radiotherapy device. Optionally, the method may include generating a quality assurance report.

Embodiments of the present disclosure may also include a method for verifying a treatment plan of a stereotactic radiotherapy device. The method may include the steps of receiving a treatment plan generated by the stereotactic radiotherapy device, applying a monte-carlo based dose generation module stored on a server system to generate a plurality of doses for locations among a target area, wherein the server system is communicatively coupled to a backend server of the stereotactic radiotherapy device, generating a second treatment plan based on the generated plurality of doses, identifying discrepancies between the received treatment plan and the generated second treatment plan, and generating a quality assurance report based on the identified discrepancies.

Generating a treatment plan may include generating a fluence map, generating a phase space map based on the generated fluence map, calculating a dose value for positions within the target area based on the phase space map, and compiling a treatment plan based on the calculated dose values. Optionally, this method may include receiving imaging data of the target area. Optionally, generating the phase space map may use beam values obtained by a compact beam scanner. Optionally, the quality assurance report may be integrated into a graphical user interface for display.

BRIEF DESCRIPTION OF THE DRAWING

For a more complete understanding of the present invention and for further features and advantages, reference is now made to the following description, taken in conjunction with the accompanying drawings, in which:

FIG. 3A illustrates results of commissioning a stereotactic radiotherapy system in accordance with some embodiments of the present disclosure.

FIG. 3B illustrates results of commissioning a stereotactic radiotherapy system in accordance with some embodiments of the present disclosure.

FIG. 3C illustrates results of commissioning a stereotactic radiotherapy system in accordance with some embodiments of the present disclosure.

FIG. 3D illustrates results of commissioning a stereotactic radiotherapy system in accordance with some embodiments of the present disclosure.

DETAILED DESCRIPTION

Embodiments disclosed herein provide a commissioned graphical processing unit (GPU) based dose generation module. In some embodiments, the dose generation module (i.e., POD-Calculator) may include a Monte-Carlo dose calculation that is configured to calculate doses by transporting particles from a phase space constructed for a stereotactic system such as a GammaPod™. The embodiments for a dose generation module may be used for commissioning, dose verification, and as a secondary dose calculation tool that is configured for performing patient specific plan quality assurance before each treatment.

In some embodiments, the dose generation module (i.e., POD-Calculator) may be a part of a POD-DOSI system and integrated with a compact beam scanner (i.e., POD-Scanner).

Figure 1:
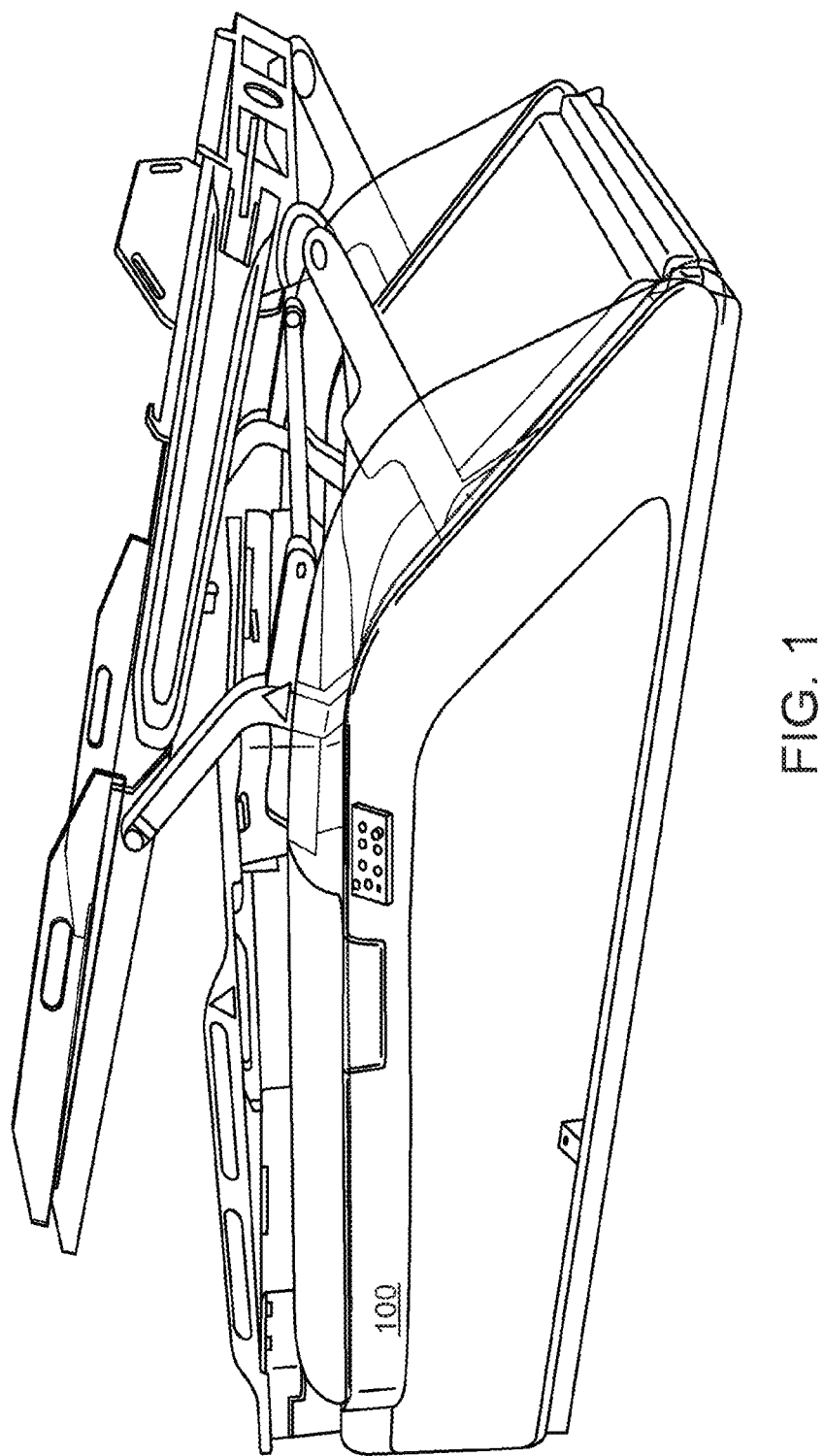
FIG. 1 illustrates a stereotactic radiotherapy system in accordance with some embodiments of the present disclosure.

FIG. 1 illustrates a stereotactic radiotherapy system, and in particular, a GammaPod™ system 100. As illustrated in FIG. 1, a patient lies in a prone position, and radiation may be applied to a target area (e.g., breast tissue). Main components of the depicted stereotactic radiotherapy system include a top shielding door, the shielding body, radiation source carrier, collimator, and patient support system, as described in Yu et al, "Gammapod-A New Device Dedicated for Stereotactic Radiotherapy of Breast Cancer", Med Phys. 40(5) (May 2013), the contents of which is hereby incorporated by reference.

Stereotactic radiotherapy systems are designed to achieve high quality breast cancer radiotherapy treatments by delivery of highly-tumoricidal doses in a short treatment course (one to five fractions), while reducing radiation damages to surrounding normal tissues. To ensure the accurate and precise dose delivery by the stereotactic radiotherapy system, it is imperative to design and follow comprehensive, rigorous protocols for initial system commissioning and routine periodic quality assurance (QA).

Commissioning is a key step prior to the clinical release of radiation delivery systems. During commissioning relevant machine and radiation beam parameters are characterized and collected to build and verify dose calculation models. Optionally, the calculation models may be used in connection with the treatment planning system (TPS) of the stereotactic radiotherapy system.

Commissioning simultaneously establishes the baseline parameters for periodic QA. QA is routinely performed to detect potential machine deviations from the commissioned standards. A comprehensive QA program includes machine mechanical/safety checks, dosimetric measurements, and patient-specific treatment plan verifications through independent dose calculations or in-phantom dose measurements.

The unique design of stereotactic radiotherapy systems such as the GammaPod™ system, and the unique features of the related treatment planning system, GammaPod™ TPS, render the relevant commissioning and QA of the GammaPod™ system less straightforward and more challenging than that for conventional teletherapy systems.

Moreover, conventional treatment planning systems may rely upon pre-calculated dose kernels in homogenous density and fixed breast cups without considering various geometry and tissues types encountered in machine commissioning, quality assurance, and patient treatment. Forward planning calculates the dose distribution for given shots as a linear combination of the pre-calculated dose kernels. Inverse planning finds the shots of optimal dose distribution for given prescription. For example, a GammaPod™ treatment plan consists of a few hundred shots delivered continuously, where a shot is depicted by its isocenter position, cone size, and delivery time. GammaPod™ performs inverse planning. For example, one particular challenge of GammaPod™ commissioning and QA is accurate calibration and evaluation of the TPS dose calculation model used by GammaPod™. In particular, conventional TPS systems such as the GammaPod™ TPS calculates dose by scaling and summing dose kernels which are pre-computed in homogenous breast tissue of mass density 0.935 g/cm$^3$. However, the commissioning, QA and patient treatments may involve various tissue types, such as water, fat, air cavity, calcifications, fiducial implants and tissue compensators. Consequently, for TPS dosimetric commissioning, conventional systems are unable to directly compare the dose measured in water with dose calculated in breast medium by GammaPod™ TPS.

Additionally, the GammaPod™ TPS can only calculate dose within a limited region (20.0×20.0×20.0 cm$^3$). Dose calculations in such a limited volume sometimes cannot fully report the doses deposited at organs-at-risks, such as the heart, lungs, the ribcage and contralateral breast, and consequently do not allow a comprehensive dose and/or volume metrics-based treatment plan evaluation and QA.

Additionally, often government regulations (i.e., U.S. Nuclear Regulatory Commission regulation I0 CFR 35.41) mandate an independent dose check for each treatment plan requiring a written directive.

Considering the circumstance in which the GammaPod™ is operated in a same-day simulation and treatment modality where treatment planning and QA are conducted while patients are waiting, and treatment is performed on the same day, measurement-based plan QA is inconvenient and adds substantial burden to the clinical workflow. In contrast, an independent secondary dose calculation system, as provided by the disclosed dose generation module, is a much more attractive alternative for patient-specific quality assurance. Conventional systems for stereotactic radiotherapies may include a treatment planning system based on pre-calculated dose kernels. However, such conventional systems may utilize Monte Carlo methods that are computationally intensive and require enormous amounts of time. Accordingly, they may not be appropriate for use in a clinical setting. For example, in the clinical setting, the time needed to verify the treatment planning system may be limited by the vacuum formed between the breast cup and a patient's breast.

Disclosed herein is a dose generation module that may be used to (i) accurately commission a stereotactic radiation therapy device such as GammaPod™ TPS, (ii) address limitations of conventional treatment planning systems such as the GammaPod™ TPS dose calculation engine, and (iii) build a comprehensive treatment plan QA system.

In an improvement over conventional systems, the disclosed systems and methods provide a dose generation module that may include a general-purpose Monte Carlo (MC)-based independent dose calculator that can handle various geometry and tissues types, such as polymethyl methacrylate (PMMA), bolus, and air cavity, encountered in machine commissioning, quality assurance (QA), and patient treatment. Utilizing the symmetry of GammaPod™'s crossfire radiation and as an independent calculator, the disclosed dose calculation models the initial photons with a uniform ellipse convolved by a Gaussian-shaped penumbra kernel for each of the two cones of GammaPod™. The ellipse size and penumbra kernel were fitted using the scanned dose profiles measured by the in-house built scanner and water cup phantom. Additionally, the disclosed dose calculation is very efficient so that it does not impede clinical workflow. The commissioned dose engine has been extensively verified and is in clinical use.

For example, the disclosed systems and methods may be used in connection with "online" calculations, or calculations performed while a patient is in the treatment room waiting for treatment delivery. While the Monte Carlo method is known for its accuracy, in conventional systems the Monte Carlo method is very time-consuming. By contrast, the disclosed system's Monte Carlo calculation is very efficient, and on the order of 1 min for plan verification. In addition, unlike measurement data, the disclosed calculation provides full volume dose distribution rather than doses at single points for dose verification. In particular, the disclosed systems are able to provide a 3D dose distribution as opposed to doses at single points.

Figure 2:
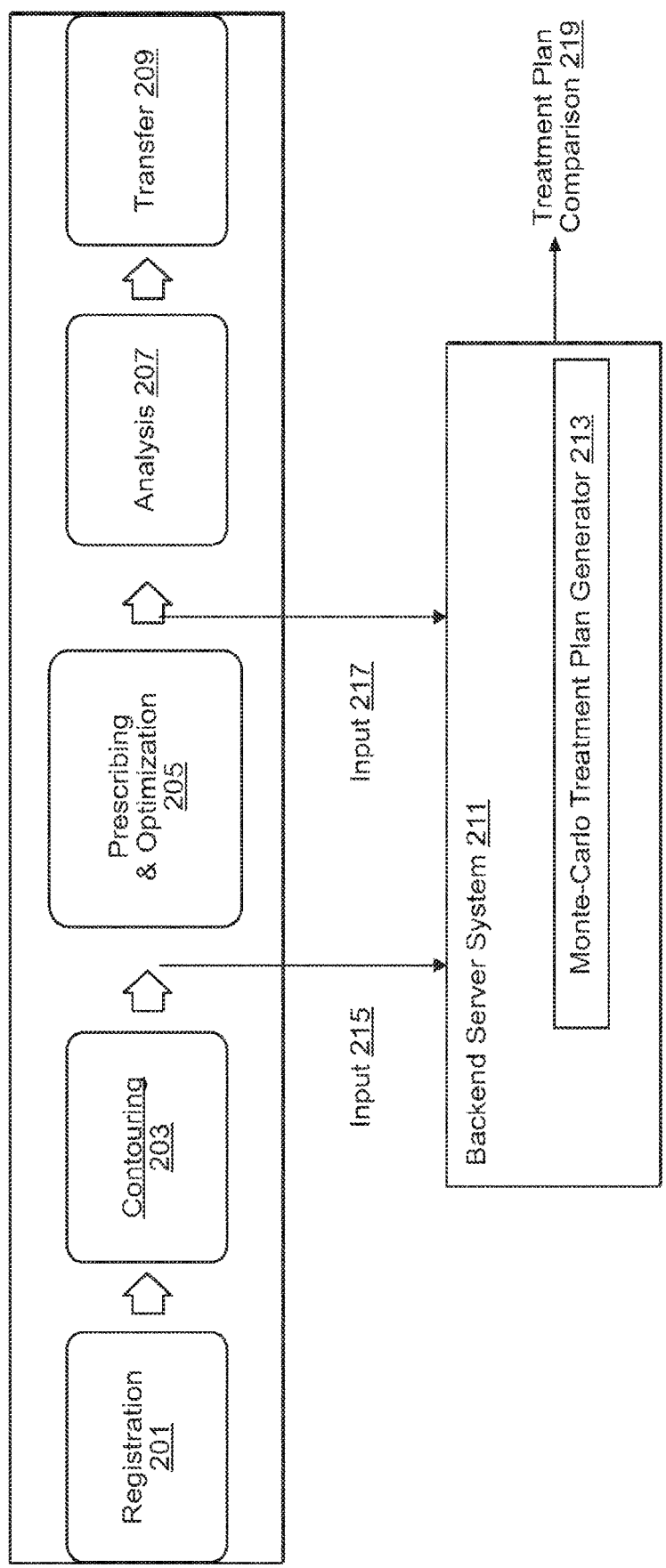
FIG. 2 illustrates the backend system used in connection with a stereotactic radiotherapy system in accordance with some embodiments of the present disclosure.

FIG. 2 illustrates the backend system used in connection with a stereotactic radiotherapy system in accordance with an embodiment of the present disclosure. In particular, the illustrated backend system for the dose generation module may be configured to perform improved and efficient Monte Carlo calculations as well as a 3D dose distribution. The dose generation module may include a general-purpose Monte Carlo (MC) dose engine calculator (i.e., POD-Calculator) that can be used for fast and accurate GammaPod™ dose calculation in various media and geometries.

In some embodiments, the disclosed dose generation module (i.e., POD-Calculator) may be used in connection with beam data obtained by a compact beam scanner (i.e., POD-Scanner). As illustrated in FIG. 2, a conventional system 200 for stereotactic radiotherapy may include the steps of registration 201, contouring 203, prescription and optimization 205, analysis 207, and transfer 209. A treatment planning system may develop a treatment plan as part of the prescribing and optimization step 205. Contouring may include obtaining computer tomography (CT) images of a region of interest 203.

The described systems and methods may provide a backend server system 211 that is configured to receive input 215 after the contouring step 203, as well as input 217 after the prescribing and optimization step 205. For example, the backend server system 211 may receive CT scans, contours and the like. In some embodiments, the received images may be in accordance with Digital Imaging and Communications in Medicine (DICOM) protocols. Additionally, the backend server system 211 may receive a treatment plan generated by the prescription and optimization 205 step.

The backend server system 211 may then apply a Monte-Carlo Treatment Plan Generator 213 to the received input 215, 217 and generate a second independent dose generation plan. In some embodiments, the Monte-Carlo Treatment Plan Generator 213 may rely upon one or more pre-calculated values. Accordingly, the time needed to generate the second independent dose generation plan may be reduced. Further, the backend server system 211 may provide a comparison between the originally generated treatment plan, and that developed by the backend server system 219. Further, in some embodiments, the results of the backend server system 211 may be integrated into a physician computing system.

In some embodiments, the backend server system 211 may be used to characterize a virtual GammaPod™ machine equipped with 25 Cobalt-60 sources housed in a hemispherical source carrier. The distance from each source to the isocenter is 380 mm. The sources are evenly spaced 1° apart in latitude from 18° to 42°, and 10° apart radially, all focusing at the isocenter.

Generation and Commissioning of Phase Space Files

In some embodiments, the Monte-Carlo Treatment Plan Generator 213 of the backend server system 211 may be used to calculate doses by transporting photons initiated from commissioned GammaPod™-specific phase space (phsp) files. The Monte-Carlo Treatment Plan Generator 213 may be used for both GammaPod™-specific phase space file generation and commissioning.

The phase space file records state information, including the type, energy, position, and direction, of all particles across a plane. The phase space file is traditionally derived by directly simulating the radiation beam transport through a machine. In order to obtain an accurate phase space file, it is necessary to simulate the beam transport through radiation subunits with complete and detailed geometry and materials information. However, end-users typically do not have machine details required for the simulation. Accordingly, phase space information and a phase space file was generated from synthetic photon fluence maps projected on the isocenter plane, as illustrated in FIGS. 3A-3D.

As illustrated in FIGS. 3A-3D, the GammaPod™ has two different cone sizes, 15 mm (see FIGS. 3C and 3D) and 25 mm (see FIGS. 3A and 3B) for beam collimation, and so two phase space files, one for each cone size, were created from two fluence maps. FIGS. 3A and 3C illustrates the synthetic fluence maps projected on the isocenter plane, for the 25 mm (FIG. 3A) and 15 mm (FIG. 3C) cones, respectively. Additionally, an illustration of the x profiles (along the x direction of the GammaPod™ coordinate) of the corresponding fluence maps (FIG. 3B for 25 mm, and FIG. 3D for 15 mm) is displayed.

Each fluence map $F(x, y)$ was modeled by convolving an elliptical function $C(x, y; w_x, w_y)$ with a Gaussian smoothing kernel $G(x, y; \sigma_x, \sigma_y)$:

$$F(x, y) = (C \otimes G);$$

$$C(x, y; w_x, w_y) = \begin{cases} 1 & \left(\frac{x^2}{w_x^2} + \frac{y^2}{w_y^2} \leq 1\right) \\ 0 & \text{(otherwise)} \end{cases}.$$

with $$G(x, y; \sigma_x, \sigma_y) = \frac{1}{\sqrt{2\pi(\sigma_x^2 + \sigma_y^2)}} \exp\left(-\left(\frac{x^2}{2\sigma_x^2} + \frac{y^2}{2\sigma_y^2}\right)\right)$$

Here, $w_x$ and $w_y$ represent the cone sizes along x (transverse) and y (vertical) directions of the fluence map, respectively. $\sigma_x$ and $\sigma_y$ are standard deviations of the Gaussian kernel along x and y directions. From the fluence map, the initial photon-projected position for the phase space file is sampled as a probability density function. The vector from the Cobalt-60 source to the projected position defines the photon transport direction for the phase space file. The photon energy from Cobalt-60 has a 50-50% probability to be one of the two levels: 1.17 and 1.33 MeV, which is also randomly sampled. Applying this approach, phase space file commissioning may be converted into fluence map commissioning, which could be further narrowed down into the commissioning of four parameters: ($w_x$, $w_y$, $\sigma_x$, and $\sigma_y$).

In a first step, to tune the four parameters (for each cone size), ten billion ($10^{10}$) initial particles may be simulated and transported on water-filled breast cup phantom CT images so that the energy deposition within each voxel may be scored. Then, the density and material maps may be extracted from the CT images with a voxel size of 1.0 x 1.0 x 1.0 mm³ and an overall dimension of 161 x 161 x 161 voxels. Then dose profiles (along x and y directions) measured in water by a compact beam scanner (i.e., POD-Scanner) may be used as the reference to tune the four fluence map parameters, until the calculated dose profiles by POD-Calculator in water match the reference ones. After that, the initial photons of the optimized fluence may be saved in phase space files for future dose calculations.

Absolute Dose Calibration

In some embodiments, the Monte-Carlo Treatment Plan Generator 213 of the backend server system 211 may be used to calibrate the absolute dose.

The absolute dosimetry of the GammaPod™ TPS is defined at the isocenter of the vendor provided PMMA phantom under the irradiation of the 25 mm cone, using the specification of dose per minute $\dot{D}_0$ at the specific commissioned date. The AAPM TG21 protocol, which allows reference dose rate calibration in water, PMMA or polyethylene may be applied to determine the reference dose. Essentially, the dose to PMMA is related to the dose measured in the ion chamber via $\dot{D}_0 = MN_{gas}(\overline{L}/\rho)_{gas}^{Med} P_{ion} P_{repl} P_{wall}$, where M is the temperature and pressure corrected electrometer reading, $N_{gas}$ is the cavity-gas calibration factor, $(\overline{L}/\rho)_{gas}^{Med}$ is the ratio of the mean restricted collision mass stopping powers of PMMA and air, $P_{ion}$, $P_{repl}$, and $P_{wall}$ are correction factors accounting for ion recombination, electron fluence changes and attenuation of chamber wall.

The Monte-Carlo Treatment Plan Generator 213, and related POD-Calculator, may use the same absolute dosimetry definition. The commissioned $\dot{D}_0$ is a fixed parameter in POD-Calculator and the delivery dose rate is the commissioned dose rate multiplied by the decay factor $\dot{D}=\dot{D}_0 * 2^{-T/t_{1/2}}$, where T is the decay time from commissioning to delivery and $t_{1/2}$=5.2714 years for Co-60. With the commissioned phase space file the dose may be calculated by transporting photons through CT image of the same PMMA phantom with vendor-provided density and material assignment. The normalization factor for the POD-Calculator may be defined as the ratio between the measured dose in the PMMA phantom and the initial calculated isocenter dose with $10^{10}$ particles for each commissioned phsp, corresponding to 25 mm and 15 mm cones. And the isocenter dose may be defined as the mean dose within a central 5 mm-diameter sphere region of interest.

The disclosed dose generation module, and POD-Calculator may be fully commissioned after phase space commissioning and normalization factor calibration. The disclosed dose generation module is capable of computing dose in different media, such as water, breast tissue, and PMMA to validate the GammaPod TPS dose engine. The absolute dose to any location of patient/phantom is calculated as $D(x) = \dot{D}\Sigma_c O_c t_c M_c(x)/M_c^0$, where x is the voxel index and c is the cone index (25 mm or 15 mm). $O_c$ is the output factor for cone c, and $t_c$ is total time with cone c open. $M_c(x)$ (in the unit of Gy/particle) is the raw MC dose per simulation particle for cone c, defined as total energy deposited at voxel x over its voxel mass. $M_c^0$ is the normalization factor for cone c, which corresponds to the MC reference dose (Gy/particle) for cone c under the commissioning condition.

Patient-Specific Plan Quality Assurance

In addition to assisting in commissioning, the dose generation module described herein may be used for patient-specific plan dose verification. Conventional stereotactic radiology treatments such as GammaPod™ may use a dynamic or continuous dose painting mode, and its treatment plans contain many radiation shots with couch movement in between. The radiation delivery and couch motion of GammaPod™ are simultaneous, synchronized and are controlled by a set of (~500) control points. Each control point is associated with a cone size, a couch position (X, Y, Z) and a time cumulating from the start of the first control point. The TPS-generated control points are finely sampled such that the couch movement between neighboring control points is small (<3 mm). With these finely sampled control points, each segment may be approximated and defined as the duration between two consecutive control points, as static.

In the dose generation module described herein, the couch position of each segment (k) may be defined as the mean of the couch positions of the adjacent control points k and k+1, and the segment time as the time difference between control points k and k+1. The dose calculated from each segment may then be added up to the total plan dose. For each plan, a fixed total number of particles ($10^9$) may be used for calculation. The number of particles assigned to each segment may be proportional to the product of the dwell time and the fluence map energy (cone-size specific), where the fluence map energy is the integration of its intensity over the entire fluence map. The number of assigned particles for each segment may be calculated as:

$$N_k = \frac{t_k A_k}{\Sigma t_k A_k} N,$$

where N is the total number of particles ($10^9$), $t_k$ is the dwell time for the $k^{th}$ segment, and $A_k$ is the fluence map energy for the cone size used in the $k^{th}$ segment.

Figure 4:
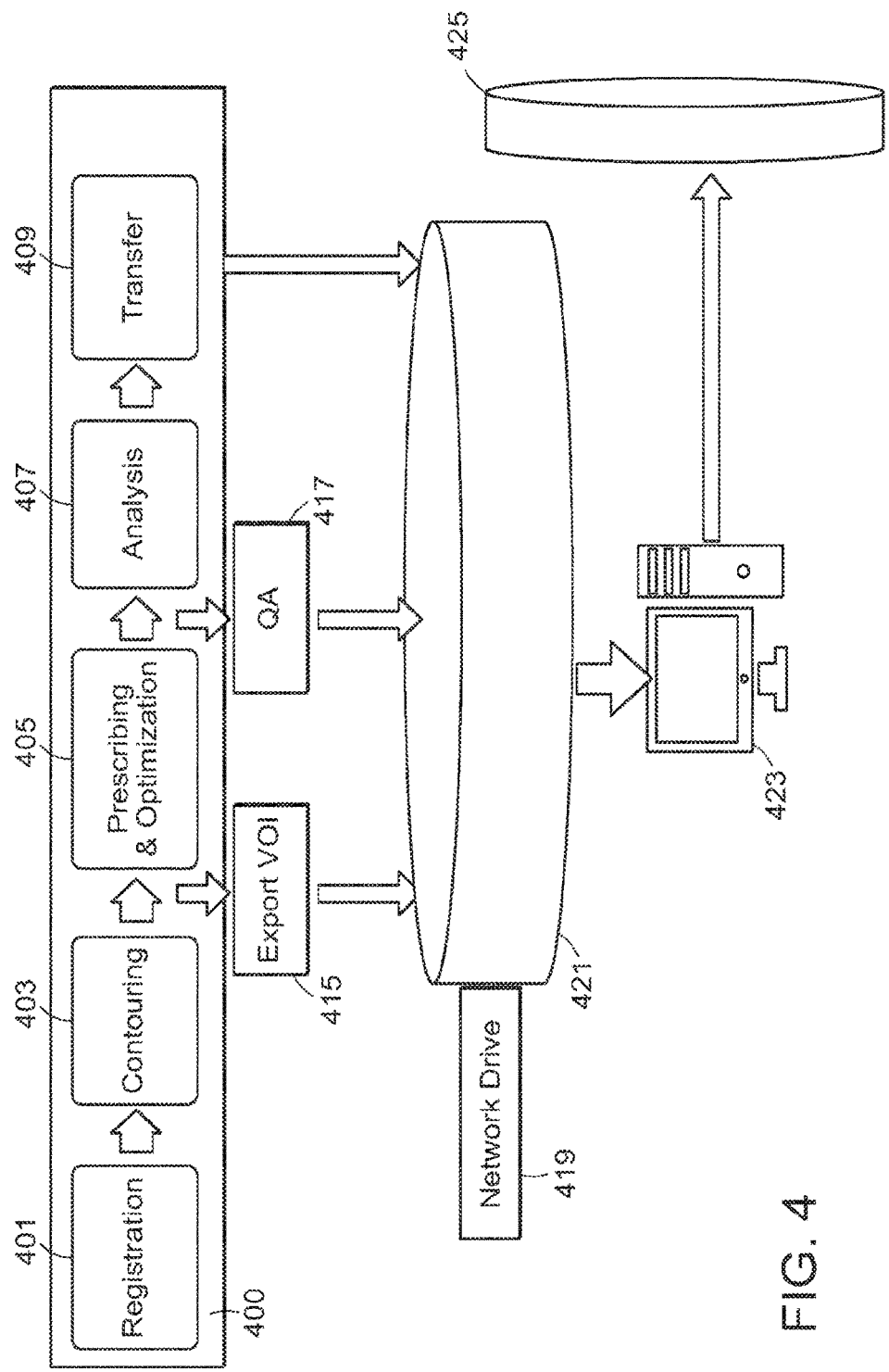
FIG. 4 illustrates the backend system used in connection with a stereotactic radiotherapy system in accordance with some embodiments of the present disclosure.

As illustrated in FIG. 4, in some embodiments, the dose generation module may be built into an software package that is configured to check plans generated by treatment planning systems and facilitate patient-specific quality assurance. For example, in some embodiments the dose generation module may be integrated into a GammaPod™ treatment workflow.

As illustrated in FIG. 4, a system 400 for stereotactic radiotherapy may include the steps of registration 401, contouring 403, prescription and optimization 405, analysis 407, and transfer 409. A treatment planning system may develop a treatment plan as part of the prescribing and optimization step 405. Contouring 403 may include obtaining computer tomography (CT) images of a region of interest.

The described systems and methods may provide a backend server system and network drive 419 that is configured to receive input 415 after the contouring step 203, as well as input 417 after the prescribing and optimization step 205. For example, the backend server system 411 may receive input 415 including CT scans, contours and the like. In some embodiments, the received images may be in accordance with Digital Imaging and Communications in Medicine (DICOM) protocols. In some embodiments the backend server system and network drive 419 may receive a volume of interest structure file.

Additionally, the backend server system 419 may receive as input 417 a treatment plan generated by the prescription and optimization 405 step. This may allow for quality assurance.

The planning CT, structures, treatment plan and dose are exported from the TPS in file formats of DICOM (CT and structures), XML and 3DDose, respectively. The treatment plan XML writes the information of control points, which includes cone size, couch position and cumulative time, and a registration matrix between the treatment machine coordinate and the patient CT image coordinate systems, which provides accurate patient geometry information for dose calculation.

The backend server system 419 may then use the dose generation module as a part of a plan check and quality assurance software 423 to apply a Monte-Carlo Treatment Plan Generator to the received input 415, 417 and generate one or more independent dose generation plans that may be used to check the treatment plan generated by the GammaPod™ TPS.

In some embodiments, the plan check software 423 may be implemented has been implemented as a background service that runs on an Alienware Aurora R8 workstation (Dell Technologies, Miami, FL) with a Titan X GPU card (NVIDIA Corporation, Santa Clara, CA).

A calculation report may automatically generated after each plan check. Different from the TPS-calculated dose distribution, the plan check software 423 including the dose generation module (i.e., POD-Calculator) may generate dose volumes covering the whole CT volume, which enables comprehensive evaluation of doses to organs-at-risk in addition to the target volumes. To fit the Monte-Carlo dose calculation into the tight clinical workflow, the CT volume may be sampled at a grid size of 2.0 x 2.0 x 2.0 mm³ from the original 1.0 x 1.0 x 1.0 mm³ resolution.

The calculation report generated by the plan check software 423 may be provided into a record and verification system 425 used to record and verify treatment plans. The plan check software 423 may be integrated into patient records, hospital records and the like.

Figure 5:
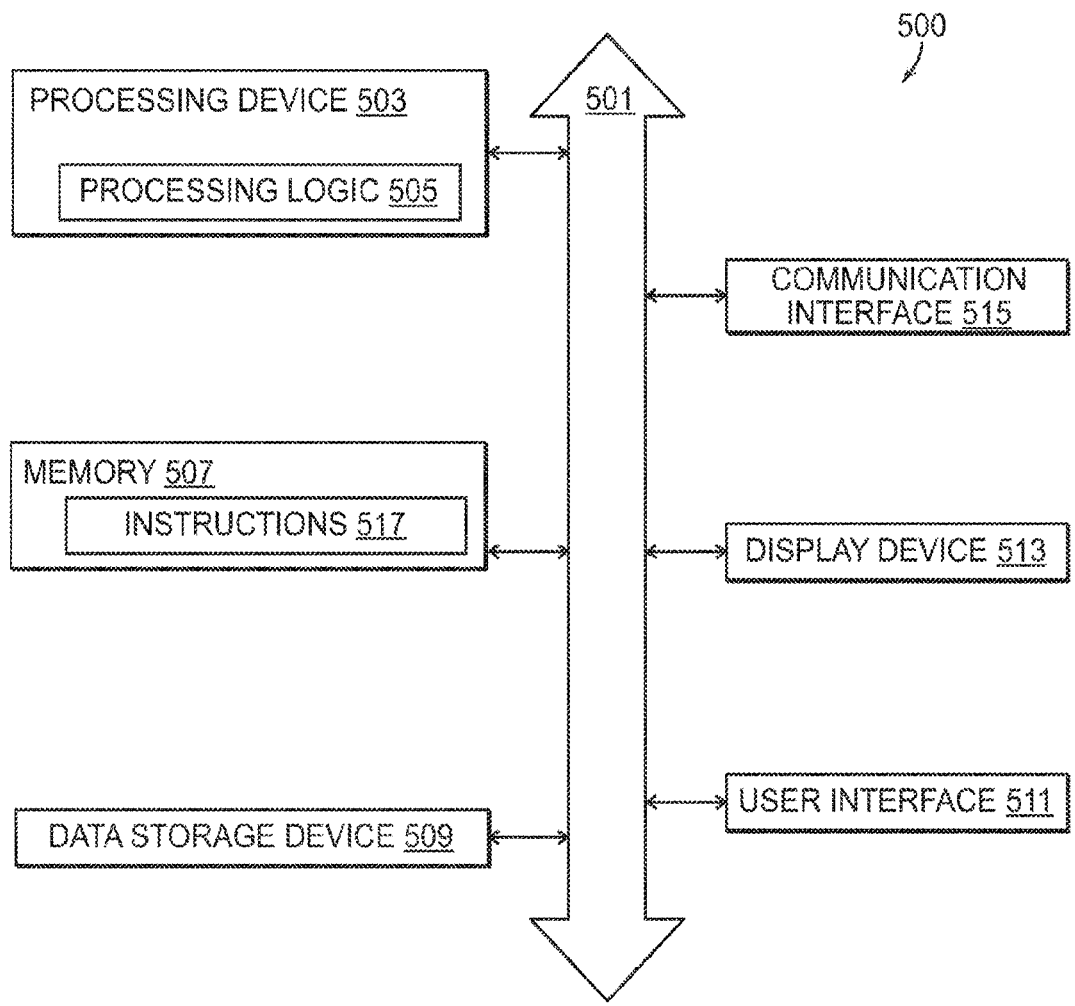
FIG. 5 illustrates a system diagram in accordance with an embodiment of the present disclosure.

FIG. 5 illustrates a system diagram in accordance with embodiments of the present disclosure. In particular FIG. 5 illustrates a functional block diagram of a machine in the example form of computer system 500, within which a set of instructions for causing the machine to perform any one or more of the methodologies, processes or functions discussed herein may be executed. In some examples, the machine may be connected (e.g., networked) to other machines as described above. The machine may operate in the capacity of a server or a client machine in a client-server network environment, or as a peer machine in a peer-to-peer (or distributed) network environment. The machine may be any special-purpose machine capable of executing a set of instructions (sequential or otherwise) that specify actions to be taken by that machine for performing the functions describe herein. Further, while only a single machine is illustrated, the term "machine" shall also be taken to include any collection of machines that individually or jointly execute a set (or multiple sets) of instructions to perform any one or more of the methodologies discussed herein. In some examples, the backend server system 211 of FIG. 2 or backend server and network drive 419 of FIG. 4 may be implemented by the example machine shown in FIG. 5 (or a combination of two or more of such machines).

Example computer system 500 may include processing device 503, memory 507, data storage device 509 and communication interface 515, which may communicate with each other via data and control bus 501. In some examples, computer system 500 may also include display device 513 and/or user interface 511.

Processing device 503 may include, without being limited to, a microprocessor, a central processing unit, an application specific integrated circuit (ASIC), a field programmable gate array (FPGA), a digital signal processor (DSP) and/or a network processor. Processing device 503 may be configured to execute processing logic 505 for performing the operations described herein. In general, processing device 503 may include any suitable special-purpose processing device specially programmed with processing logic 505 to perform the operations described herein.

Memory 507 may include, for example, without being limited to, at least one of a read-only memory (ROM), a random access memory (RAM), a flash memory, a dynamic RAM (DRAM) and a static RAM (SRAM), storing computer-readable instructions 517 executable by processing device 503. In general, memory 507 may include any suitable non-transitory computer readable storage medium storing computer-readable instructions 517 executable by processing device 503 for performing the operations described herein. Although one memory device 507 is illustrated in FIG. 5, in some examples, computer system 500 may include two or more memory devices (e.g., dynamic memory and static memory).

Computer system 500 may include communication interface device 511, for direct communication with other computers (including wired and/or wireless communication), and/or for communication with network. In some examples, computer system 500 may include display device 513 (e.g., a liquid crystal display (LCD), a touch sensitive display, etc.). In some examples, computer system 500 may include user interface 511 (e.g., an alphanumeric input device, a cursor control device, etc.).

In some examples, computer system 500 may include data storage device 509 storing instructions (e.g., software) for performing any one or more of the functions described herein. Data storage device 509 may include any suitable non-transitory computer-readable storage medium, including, without being limited to, solid-state memories, optical media and magnetic media.

Experimental Data

In some embodiments, the dose generation module described herein may use GammaPod™ beam data collected by a compact beam scanner (i.e., POD-Scanner) to commission the dose generation module (i.e., POD-Calculator) by using water as the medium. After the dose generation module is commissioned, the calculation medium may be switched from water to breast in the dose generation module (i.e., POD-Calculator), to commission and evaluate the GammaPod™ treatment planning system (TPS).

End-to-end tests were also performed using the combined dosimetry system including the compact beam scanner and dose generation module (i.e., POD-DOSI: POD-Scanner and POD-Calculator) to compare plan doses between the POD-Calculator, GammaPod™ TPS, and in-water ion chamber measurements.

After commissioning, the POD-Calculator was integrated into an independent, secondary dose calculation framework to perform patient-specific treatment plan QA for routine clinical practice.

Clinical Example #1: GammaPod™ Commissioning

In some embodiments, the systems and methods described herein related to the compact beam profile scanner (the POD-scanner) were integrated into a two-part system (POD-Scanner and POD-Calculator), that provides dedicated dosimetry system for accurate and efficient commissioning and QA of GammaPod™ including beam profile scanning and TPS validation. In-water beam profiles were automatically acquired by the POD-Scanner, and subsequently fed into the POD-Calculator to commission the phase space file. After commissioning, the POD-Calculator can switch the calculation medium from water to breast tissue. As a result, beam profiles in the breast medium were used to commission and evaluate the GammaPod™ TPS in accordance with the schematic depicted in FIG. 6.

Figure 6:
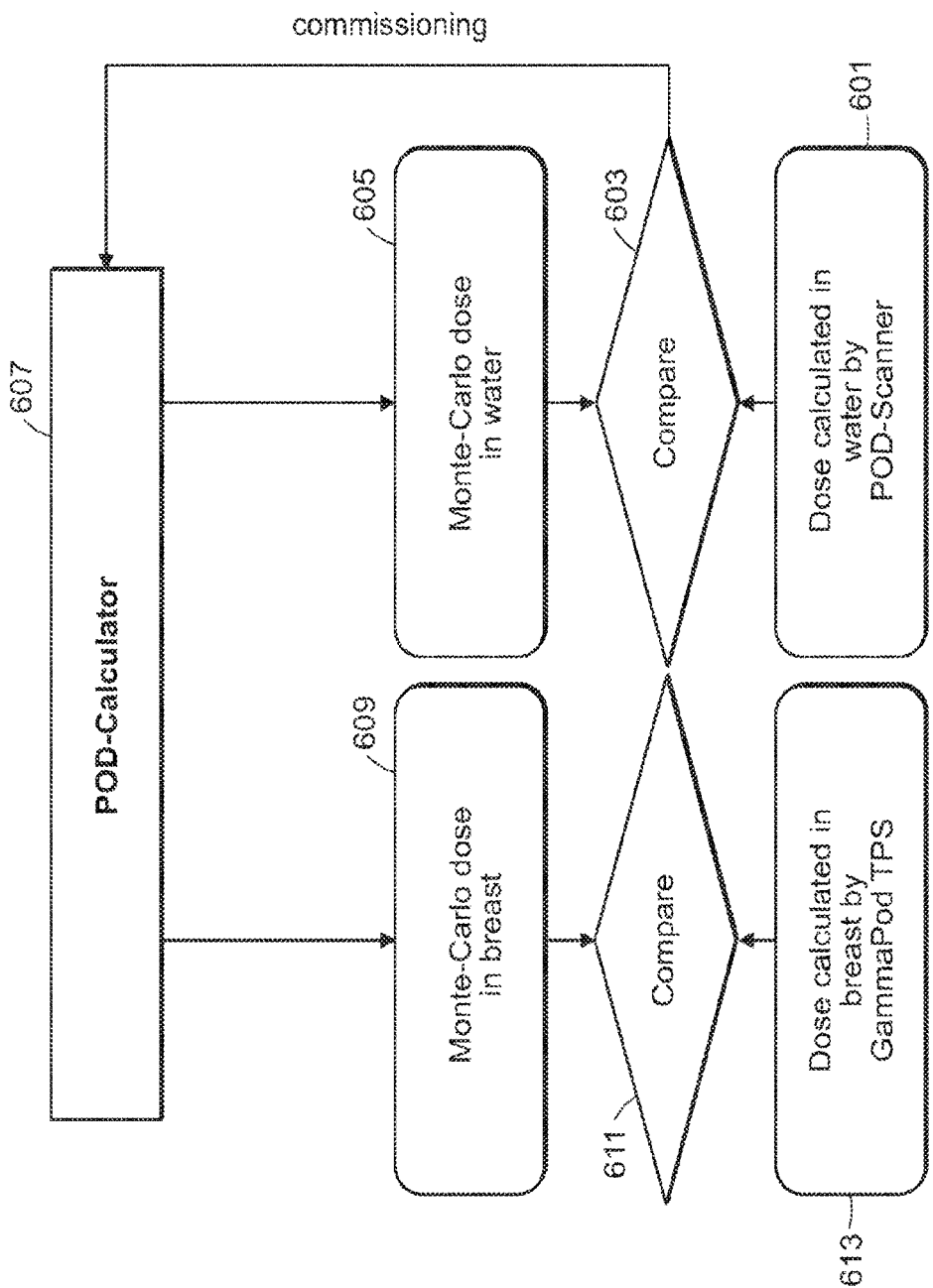
FIG. 6 illustrates an experimental setup for a stereotactic radiotherapy system in accordance with some embodiments of the present disclosure.

As illustrated in FIG. 6, doses were measured in water by the compact beam profile scanner or POD-Scanner 601 were compared 603 to a dose calculated by monte-carlo methods 605 and used for the commissioning of a calculator or dosimetry system 607. Similarly, a monte-carlo dose for breast tissue 609 calculated by the calculator or dosimetry system 607 is compared 611 to a dose for breast tissue provided by the GammaPod™ Treatment Planning System 613.

As illustrated in FIG. 6, in addition to the beam profile comparison, the POD-Calculator or dosimetry system 607 and the compact beam profile scanner or POD scanner were integrated to conduct end-to-end tests.

Each end-to-end test was featured with CT image acquisition, image exporting/importing, stereotactic system coordinates registration, target contouring, treatment planning, secondary dosimetry check and plan-specific QA. Since the GammaPod™ system provides 26 breast cups for treatment, each with a different size, the end-to-end tests were conducted on these 26 water-filled breast cup phantoms. In-water dose measurements via the POD-Scanner were compared with in-water dose calculations via the POD-Calculator and compared the corresponding in-breast dose calculations via the POD-Calculator with the in-breast dose calculations via the GammaPod™ TPS. In total, 56 different plans were generated to verify the GammaPod™ TPS and the commissioned POD-Calculator dose engine. The planning target volumes (PTVs) of these 56 end-to-end testing plans ranged from 1.91 cc to 63.18 cc and placed randomly inside breast cups. The prescribed dose ranged from 4 Gy to 25 Gy in 1 fraction and dose distribution were normalized to 95% of PTV covered by 100% of the prescription dose. Considering the quick dose fall-off of a GammaPod™ plan and distal critical structures (e.g. heart and lung), in these 56 plans, dose constraints were not imposed. Thus, these plans were desired for dosimetry measurement and comparison rather than plan quality evaluation.

Commissioning the Dose Generation Module (POD-Calculator)

Figure 7:
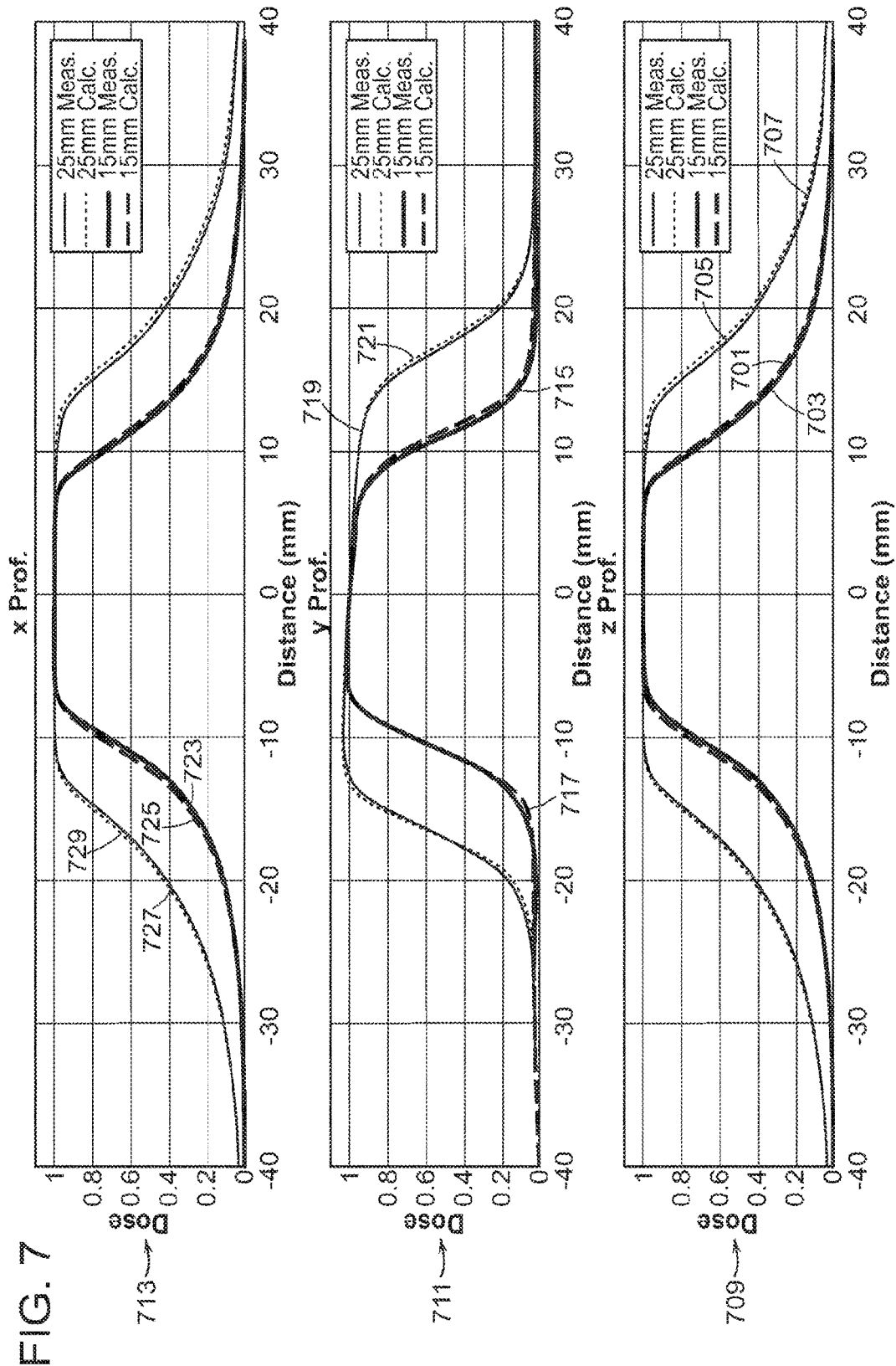
FIG. 7 illustrates an experimental result for a stereotactic radiotherapy system in accordance with some embodiments of the present disclosure.
Figure 8:
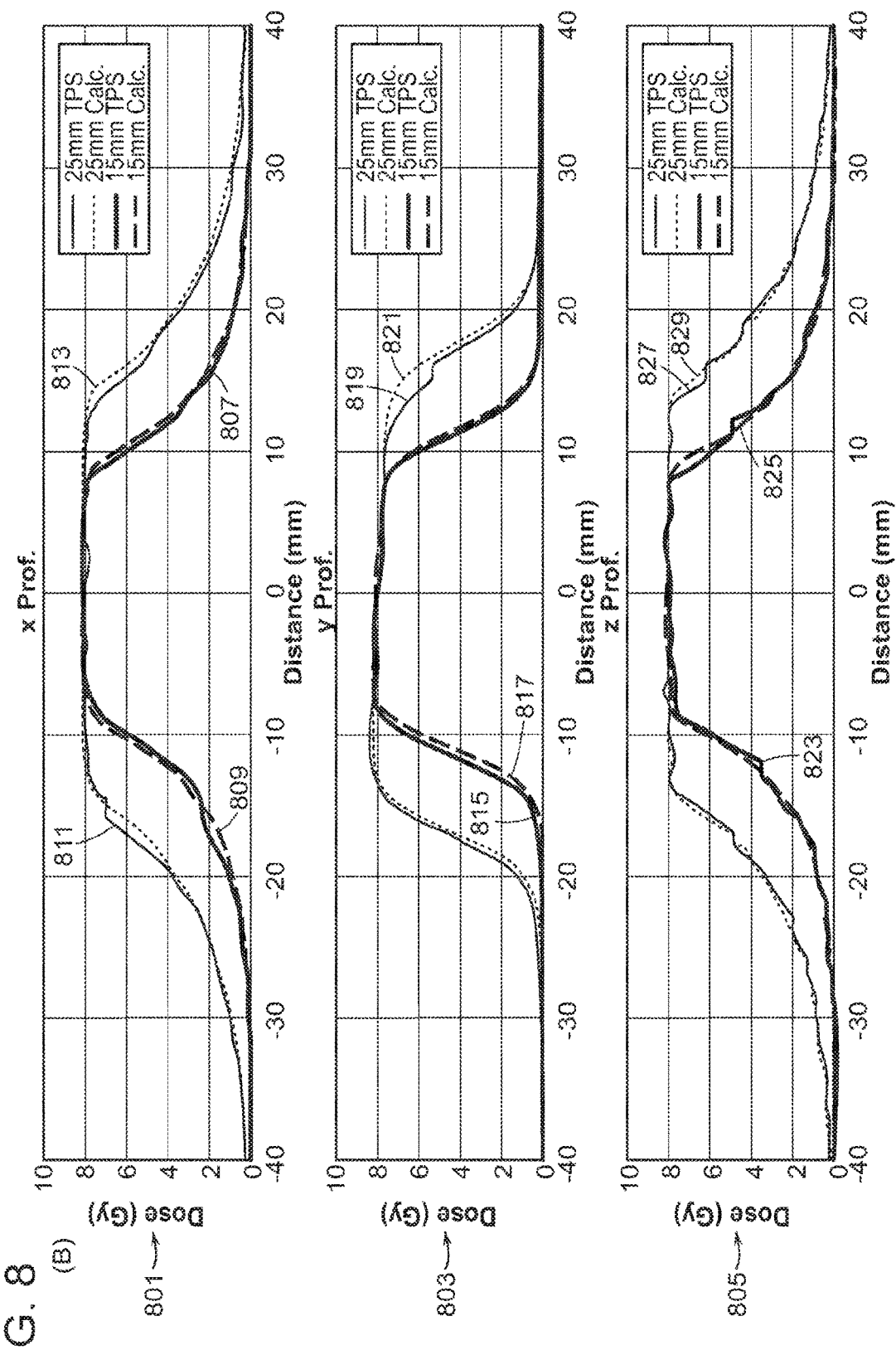
FIG. 8 illustrates an experimental result for a stereotactic radiotherapy system in accordance with some embodiments of the present disclosure.

As illustrated in FIGS. 7 and 8, the dose generation module may be commissioned using the procedures discussed above.

In particular, for the 25 mm cone, the commissioned effective fluence map parameters were $w_x=w_y=30.0$ mm and $\sigma_x=\sigma_y=1.5$ mm. The corresponding parameters for the 15 mm cone were $w_x=w_y=19.5$ mm and $\sigma_x=\sigma_y=1.5$ mm. The effective fluence map width was 5.0 mm (4.5 mm) larger than the nominal size of the 25 mm (15 mm) cone, which was contributed from the finite source size. The $\sigma_x=\sigma_y=1.5$ mm corresponded to the geometrical penumbra of the collimator system. The corresponding lateral and vertical profiles had full width at half maximum (FWHM) values of 38.1 mm and 34.8 mm for the 25 mm cone, and 24.7 mm and 22.4 mm for the 15 mm cone.

FIG. 7 illustrates a comparison between the beam profiles in water calculated by the POD-Calculator and the beam profiles measured by the POD-Scanner. As illustrated in FIG. 7, the calculated profiles from the dose generation module or POD-Calculator matched well with the water phantom measurements to <0.5 mm accuracy, so did the profiles from the POD-Calculator and the GammaPod™ TPS. Illustrated are the profiles across the x-axis 713, y-axis 711, and z-axis 709. In particular the TPS measured values for the 15 mm cone 701, 715, 723, were close to that calculated by the dose generation module 703, 717, 715. Similarly, the TPS measured values for the 25 mm cone 705, 719, 727 were close to that calculated by the dose generation module 707, 721, and 729.

FIG. 8 illustrates a comparison between the absolute dose profiles in breast calculated by the POD-Calculator and the TPS. Illustrated are the profiles across the x-axis 801, y-axis 803, and z-axis 805. In particular the TPS measured values for the 15 mm cone 823, 815, 807, were close to that calculated by the dose generation module 825, 817, 809. Similarly, the TPS measured values for the 25 mm cone 827, 819, 811 were close to that calculated by the dose generation module 829, 821, 813.

As illustrated in FIG. 8, the profiles from the GammaPod™ TPS were less smooth than the dose profiles calculated by the POD-Calculator, due to the limited dose grid resolution employed by the GammaPod™ TPS (5.0 x 5.0 x 5.0 mm).

Absolute Dosimetry

On the commissioning date the reference dose rate of the 25 mm cone ($\dot{D}_0$) was 3.12 Gy/min, while dose rate for 15 mm cone was 2.93 Gy/min, which resulted $O_{c=25mm}=1.0$ and $O_{c=15mm}=0.94$. The same absolute dosimetry was adopted in POD-Calculator with the measured dose-rate and commissioning date as fixed parameters.

Figure 9B:
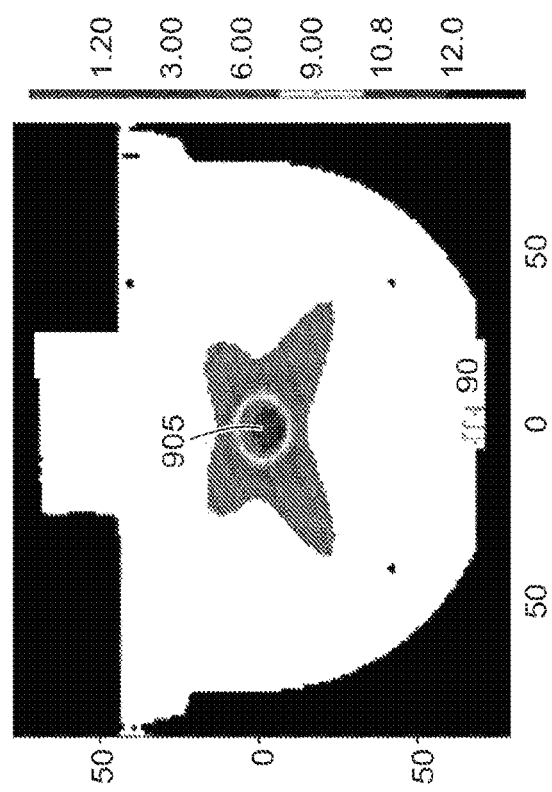
FIG. 9B illustrates an experimental result for a stereotactic radiotherapy system in accordance with some embodiments of the present disclosure.
Figure 9A:
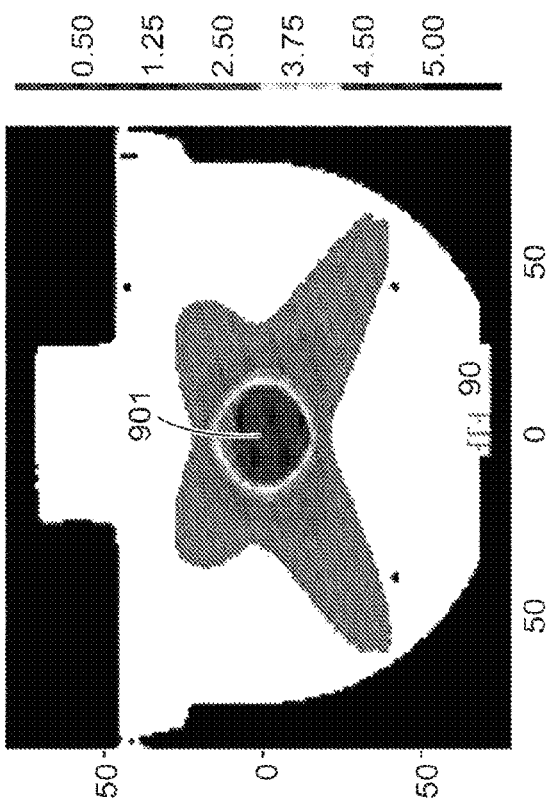
FIG. 9A illustrates an experimental result for a stereotactic radiotherapy system in accordance with some embodiments of the present disclosure.

FIGS. 9A and 9B show 9A and 9B shows the results of absolute dose calculation with $10^{10}$ particles using 25 mm (left, FIG. 9A) and 15 mm (right, FIG. 9B) cone. The mean doses from the central 5 mm sphere (indicated as circle, 901, 905) are used to determine the normalization factor for 25 mm and 15 mm cone, respectively.

The calculated normalization factor is $M_{c=25mm}^0=5.329\times 10^{-13}$ Gy/particle for 25 mm cone and $M_{c=15mm}^0=1.286\times 10^{-12}$ Gy/particle for 15 mm cone. Here $M_c^0$ is defined as isocenter dose per sampled particle. Note that $M_{c=25mm}^0$ is smaller than $M_{c=15mm}^0$. This is because the effective fluence map area of 25 mm cone is larger than that of 15 mm cone. For the same ($10^{10}$) particles per cone sampled, a single particle sampled from 25 mm cone fluence map is more likely to be from outer region and has less contribution to the isocenter dose than that from 15 mm cone.

FIGS. 9A and 9B show absolute monte-carlo dose on a PMMA phantom for 25 mm (left, FIG. 9A) and 15 mm (right, FIG. 9B) cones with $10^{10}$ particles simulated. The unit of dose is in mGy and the unit of distance is in mm. The circles 901, 905 shows the central 5 mm diameter sphere region of interest to calculate the monte-carlo normalization factor.

Statistical Uncertainties

Single shot simulation was used to quantify the statistical uncertainty (simulation precision) of monte-carlo simulation in the dose generation module or POD-Calculator. For each of two cone sizes (25 mm and 15 mm), the uncertainty at each voxel 6 normalized by its corresponding voxel dose was calculated. The relative uncertainty over the high dose region where the local dose exceeds half of the dose at isocenter, i.e. volume enclosed by the 50% isodose line was further averaged. The quantity $\overline{(\sigma/D)_H}$ indicates the simulation precision in the high dose region. The simulation precision $\overline{(\sigma/D)_H}$ with a 1.0 x 1.0 x 1.0 mm$^3$ voxel size and $10^9$ particle histories are 0.8% (0.6%) for a single 25 mm (15 mm) cone shot. The volumes enclosed by the 50% isodose line is 24.6 cc (6.9 cc) for a 25 mm (15 mm) cone shot respectively. As clinical GammaPod™ plans typically combine 25 mm and 15 mm cones with the target volume as large as 100 cc, simulation of $10^9$ particle histories is required to achieve a simulation precision $\overline{(\sigma/D)_H}$ of 1% for a 2.0 x 2.0 x 2.0 mm$^3$ voxel size. Accordingly, $10^9$ particle histories for secondary dose calculations of patient-specific plan QA were used.

POD-Calculator for Patient-Specific Plan QA

For independent plan QA, the total elapsed time from TPS plan export to QA report generation is approximately five minutes. During this time only one minute is used to calculate the $10^9$ particle histories, with majority of time spent on data export and transfer between the GammaPod™ TPS computer and the plan check server. The plan QA report consists of multiple tables and figures to summarize independent calculation and plan verification results. In some embodiments the QA report includes dosimetric comparison between TPS and PODCalc results, Gamma Index analysis of the discrepancy and whether or not each target or organ-at-risk meets radiation therapy and oncology group and clinical trial criteria.

Figure 10A:
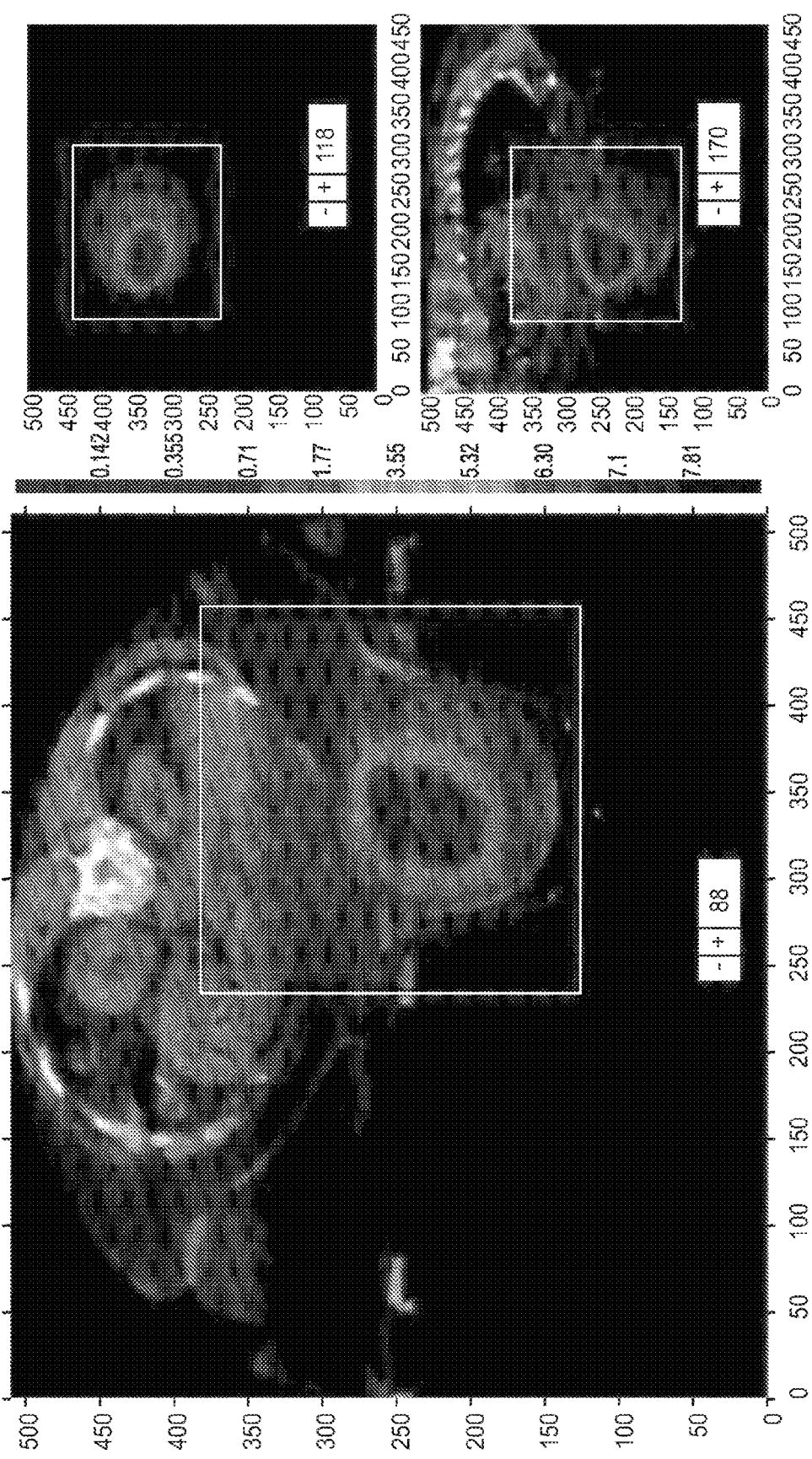
FIG. 10A illustrates an experimental result for a stereotactic radiotherapy system in accordance with some embodiments of the present disclosure.
Figure 10B:
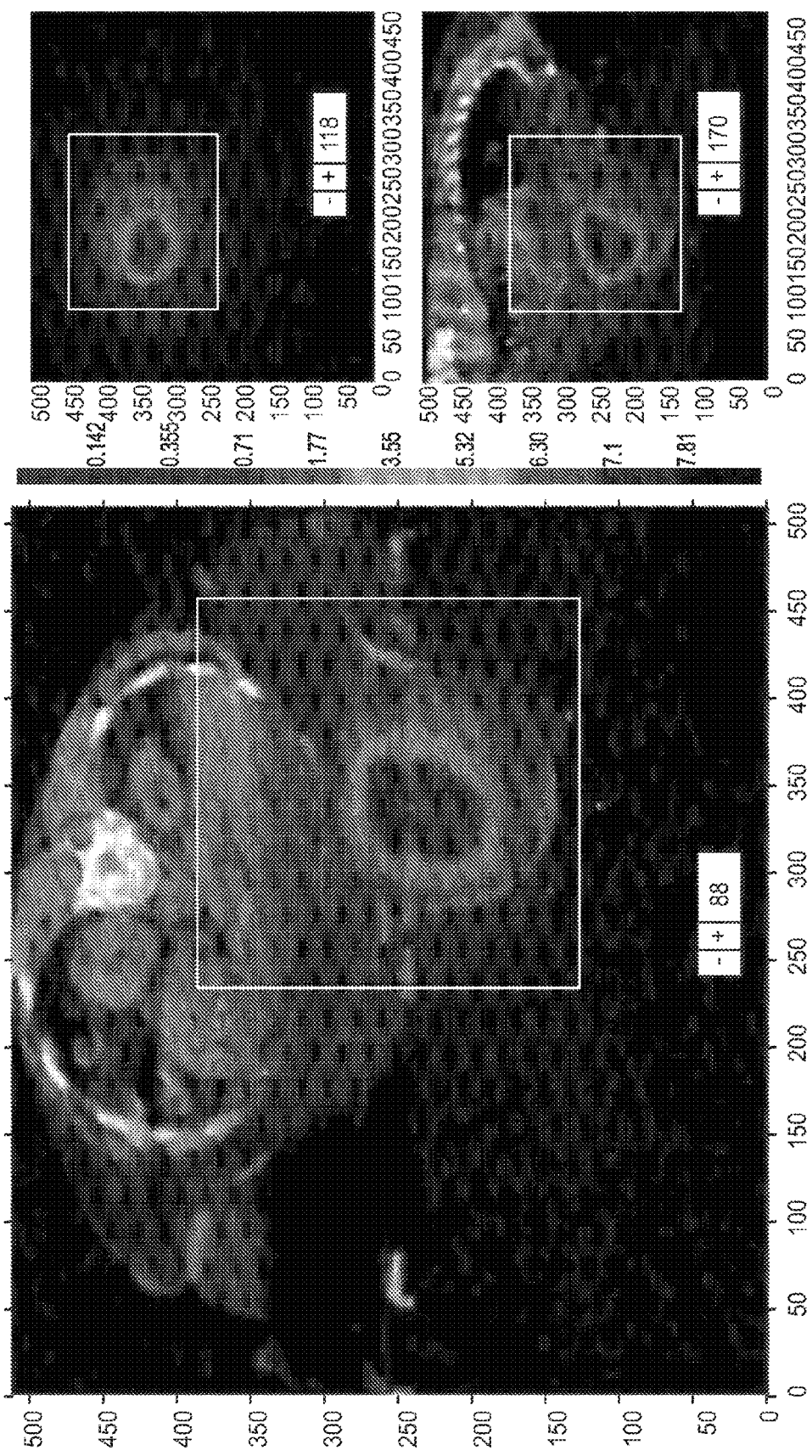
FIG. 10B illustrates an experimental result for a stereotactic radiotherapy system in accordance with some embodiments of the present disclosure.
Figure 10C:
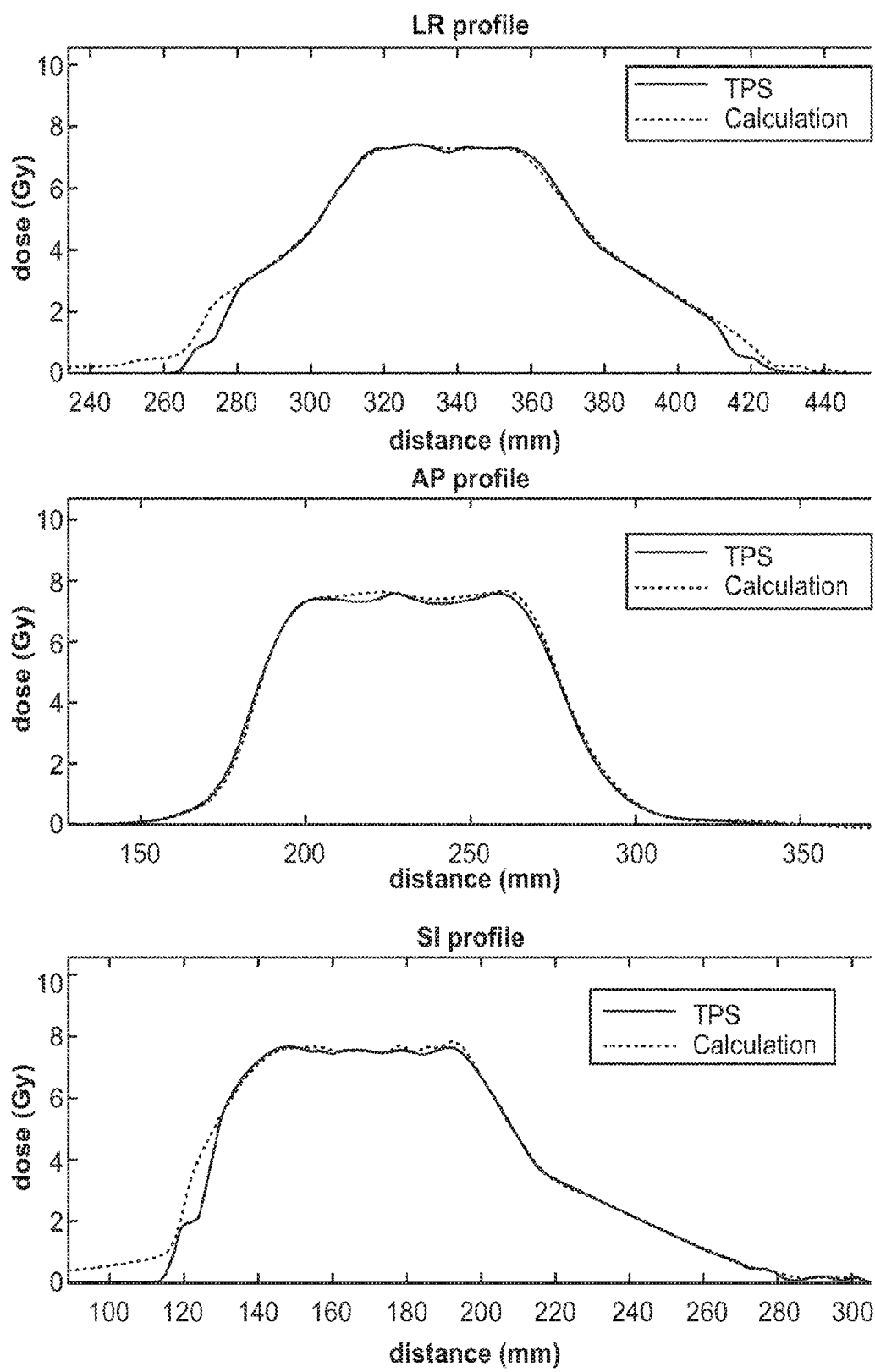
FIG. 10C illustrates an experimental result for a stereotactic radiotherapy system in accordance with some embodiments of the present disclosure.

FIGS. 10A-10C illustrate figures from a clinical case. In particular FIG. 10A illustrates 3D dose distribution maps exported from the GammaPod™ TPS for a clinical plan. FIG. 10B illustrates 3D dose distribution from the POD-Calculator for the same plan. FIG. 10B provides a comparison between dose profiles generated by the GammaPod™ TPS and the POD-Calculator, along left-right, anterior-posterior and superior-inferior directions (patient coordinate), respectively. All profiles went through the center of tumor.

As demonstrated, the POD-Calculator reports dose across the entire CT, some of which is not covered by the GammaPod™ TPS. The 3D Gamma passing rate (2 mm/2% criteria) is also computed for each case between the GammaPod™ TPS- and the POD-Calculator-calculated dose, which is 96.7% for the case reported in FIGS. 10A-10C.

End-to-End Tests Results

For the end-to-end tests featuring 56 different plans, the planned point-doses (measured by a compact beam scanner such as the POD-Scanner) in water were within ±2.20% of the doses calculated by POD-Calculator in water (range: −2.01% to 2.20%, mean: 0.04%, std_dev: 1.10%). Correspondingly, when switching the calculation medium from water to breast, the POD-Calculator point doses were within ±1.60% of the GammaPod™ TPS-reported doses (range: −1.59% to 1.51%, mean: −0.02%, std_dev: 0.73%). The average 3D gamma passing rate between the GammaPod™ TPS dose and the POD-Calculator dose for in-breast calculations of the 56 plans was 97.10±1.8% under the 2%/1 mm gamma criteria. Note that a stricter 2%/1.0 mm gamma criteria for commissioning and end-to-end test was used and the criteria was relaxed to 2%/2 mm for routine patient-specific QAs.

Figure 11C:
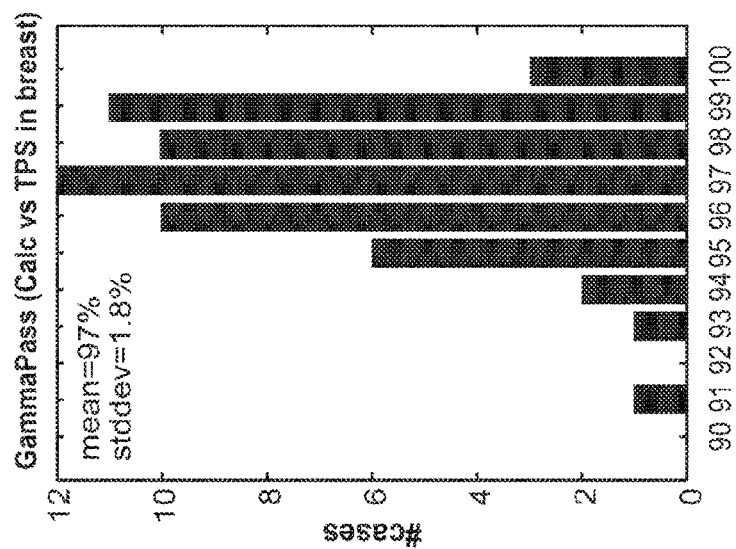
FIG. 11C illustrates an experimental result for a stereotactic radiotherapy system in accordance with some embodiments of the present disclosure.
Figure 11B:
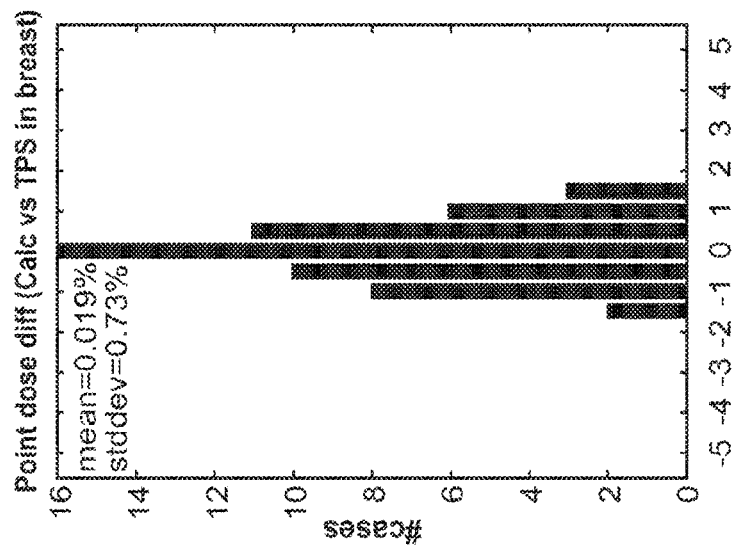
FIG. 11B illustrates an experimental result for a stereotactic radiotherapy system in accordance with some embodiments of the present disclosure.
Figure 11A:
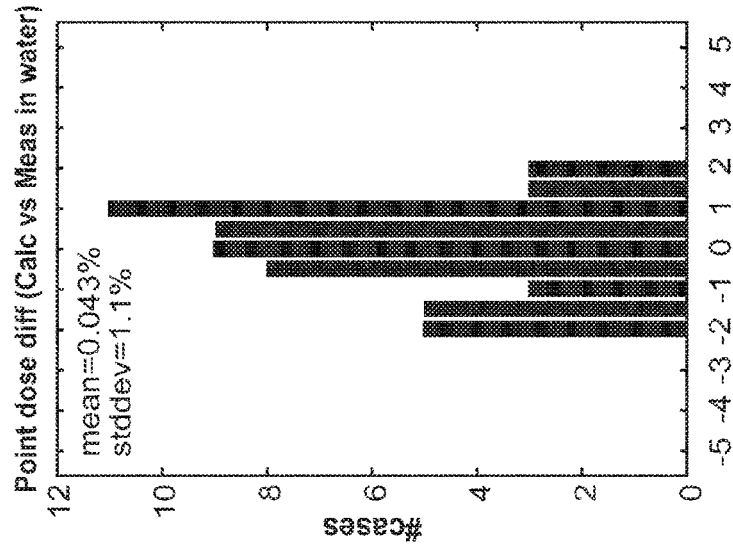
FIG. 11A illustrates an experimental result for a stereotactic radiotherapy system in accordance with some embodiments of the present disclosure.

Results are presented in FIGS. 11A-11C which provide distribution statistics of point dose differences and gamma passing rates generated based on 56 different GammaPod™ plans designed on 26 water-filled breast cup phantoms. In FIG. 11A, the X-axis displays dose differences between POD-Scanner measured point-doses in water and POD-Calculator calculated point-doses in water: (Calc−Meas)/Meas, while the Y axis displays case number distributions. In FIG. 11B, the X-axis displays dose differences between GammaPod™ TPS calculated point-doses in breast and POD-Calculator calculated point-doses in breast: (Calc−TPS)/TPS while the Y-axis displays case number distributions. In FIG. 11C, the X-axis displays Gamma passing rates (2%/1 mm) between GammaPod™ TPS calculated 3D-doses in breast and POD-Calculator calculated 3D-doses in breast and the Y-axis displays case number distributions.

Clinical Example #2: Independent Dose Calculation for GammaPod™ Treatment Purpose GammaPod™ is the first stereotactic body radiation therapy system optimized for breast cancer treatment. Its treatment planning system (TPS) uses dose kernels pre-calculated in homogenous density and fixed breast cups. However, the commissioning, QA, and patient treatment may involve various geometry and tissue types, such as PMMA, water, air cavity, bolus. Accordingly, a general-purpose Monte Carlo (MC)-based independent dose calculator is needed for routine clinical use of GammaPod™

Material and Methods

Due to symmetry of GammaPod™'s crossfire radiation and as an independent calculator, a fluence map was used instead of the phase space to model the initial photons with a uniform ellipse convolved by a Gaussian-shaped penumbra kernel for each of the two cones on GammaPod™. The ellipse size and penumbra kernel were fitted using the scanned dose profiles measured by the in-house built scanner and water cup phantom. The commissioned dose engine was then verified by point dose measurements for 56 different plans in 26 water cups. The calculation engine is implemented as a background service and automatically generates a second dose calculation report after each GammaPod™ plan export.

Results

The second dose calculation took less than 1 minute with 1-billion particles when running on a Titan-X GPU workstation. The commissioned effective fluence has 19.5 mm and 30 mm ellipse sizes with the same penumbra (sigma=1.5 mm) and 24 mm and 37.5 mm dosimetric cone sizes (FWHM) for the 15 mm and 25 mm cones, respectively. The second dose had <0.3 mm and <2% difference from measured profiles and point dose for commissioning and plan verifications, respectively, and had a 3D gamma pass rate >90%(2%/1 mm) against the TPS dose for breast.

Conclusions

A general-purpose MC dose engine for GammaPod™ was developed and validated. With proper commissioning and data-flow management, it has been integrated into the clinical workflow as a patient-specific QA tool for GammaPod™

Clinical Example #3: GammaPod™ Independent Dose Calculation Significance/Clinical Impacts The GammaPod™ treatment planning system (TPS) uses dose kernels that are pre-calculated on homogenous density, in a set of fixed-size cups. However, as commissioning, QA, and patient treatment may involve various geometry and tissue types, including PMMA, water, air cavity, bolus, etc., a general-purpose independent dose calculator is needed for routine clinical use of GammaPod™. The disclosed systems and methods provide an innovative and significant improvement as it is the first approach to build full Monte Carlo (MC) dose calculation engine that can be applied to any breast/phantom geometry and materials.

Results

An independent, second dose calculator was commissioned using the scanned dose profiles measured by the in-house built PodPhantom (a stereotactic radiography system) and profile scanner. The commissioned dose engine is then verified by water cup point dose measurements of 56 different plans in 26 various cup size and TPS dose calculation in breast. The dose comparison shows that 2nd dose calculation against measurement for both in water and breast are within ±2%, and the 3D Gamma Pass Rate comparing 2nd dose against TPS dose are >90% using the 2%/1 mm criteria.

In some embodiments, the systems and methods described herein for a dose generation module may be used in connection with a GammaPod™ system. The GammaPod™ system provides a dedicated tool for highly-focused stereotactic breast radiation therapy, which could potentially help to increase the therapeutic ratio by escalating dose to the tumor and reducing dose to surrounding healthy tissues. The single- and hypo-fractionated treatment regimens could also potentially improve patient convenience and reduce the medical cost. However, a rigorous commissioning and QA protocol needs to be established to ensure the safety and stability of the system before clinical release. The systems and methods described herein, including the dose generation module, may be used alone or in combination with a compact beam scanner (i.e., POD-Scanner) for GammaPod™ commissioning and patient-specific QAs.

A compact beam scanner (i.e., POD-Scanner) may allow for automatic radiation detector navigation from outside the vault and avoids interruptions to beam profile and point dose acquisitions. Using such a system substantially reduces the beam profile acquisition time (less than two days, as compared to greater than one month).

The dose generation module (i.e., POD-Calculator) described herein adopts a Monte-Carlo (MC) dose calculation engine and calculates dose using phase space files, which were generated on synthetic photon fluence maps by convolving an elliptical function C(x, y; $w_x$, $w_y$) with a Gaussian smoothing kernel G(x, y; $\sigma_x$, $\sigma_y$). Such synthetic function has the advantage of flexibility, because of its capability of modeling machine physical geometry, e.g. source numbers changes via adjusting function parameters ($w_x$, $w_y$, $\sigma_x$, and $\sigma_y$).

Because of the use of synthetic functions, the dose generation module described herein is capable of adjusting to changes in the physical geometry of the underlying stereotactic radiotherapy device. For example, while the first generation of the GammaPod™ system contains 36 sources with each source 1° apart in latitude from 18° to 53°, and 10° apart radially. To decrease the dose to the heart, the second generation of GammaPod™ system[10] removes the 11 sources at highest latitudes (43° to 53°) and reduces the total source number to 25. However, the dose generation module described herein is capable of calculating accurate dose for both GammaPod™ generations without remodeling phase space files from scratch, but by instead adjusting parameters of synthetic fluence maps function.

As described herein, the dose generation module plays an important role in the commissioning of stereotactic radiotherapy devices. Further, the dose generation module allows for the secondary dose calculations for plans and for the direct comparison with plans produced by the treatment planning system. It also allows calculation medium switching to directly compare with measurements performed in water and in PMMA.

In some embodiments, the dose generation module or POD-Calculator described herein also plays a role as an independent dose calculation engine specific to the GammaPod™ system and functions as a secondary dose calculation engines.

In some embodiments, the dose generation module may be integrated into the clinical workflow for patient-specific plan QA which also promotes the safety of the treatments and the efficiency of clinical workflow.

In some embodiments, generating a treatment plan may include defining dosimetric objectives and constraints for a target area and organs-at-risk. The system may assign initial locations for the plurality of spots within a target area. The system may then repetitively: calculate the dose contribution from the plurality of spots, evaluate the objective function and its derivative, and update the spot position and intensity according to the objective value and derivative. The process may be repeated until a treatment plan is generated.

In conventional stereotactic radiotherapy systems such as the GammaPod™ patients' breasts are immobilized via a vacuum system in the breast cup from CT simulation to the end-of-treatments. Prolonged vacuum time increases the potential risk of losing the suction maintained by the vacuum system and disrupting the immobilized position of the breast, which warrants re-starting the whole simulation-treatment process and would severely impact the clinical efficiency. Thus, a fast secondary check for patient-specific QA is necessary. The current solution provided by the vendor for patient-specific QA, which maps the plan to a polyethylene phantom and requires a full delivery and measurement using the phantom, significantly prolongs the vacuum time and is less desirable as compared to our solution. By contrast, the dose generation module described herein and its related application for quality assurance enables the generation of a treatment plan QA report within a five minutes overhead, with the majority of time spent on data transfer between systems. Accelerating the transfer speed can further boost plan QA efficiency. Nevertheless, this five minute overhead can also be overlapped with other activities such as treatment report generation and physician plan approval, rendering only marginal interference to the treatment flow of the patient.

In addition to plan QA, the dose generation module described generates a much larger dose reporting region as compared to the treatment planning system of conventional systems. This allows for the detailed, accurate reporting of organ-at-risk dose to comprehensively evaluate a clinical plan.

The disclosed compact beam scanner and dosimetry system (i.e., the POD-DOSI system) meets the challenge of GammaPod™ commissioning and QA, to improve the efficiency, accuracy and safety for commissioning and routine clinical treatments. The developments can potentially be used at other centers, to coordinate streamlined and homogeneous commissioning and QA practices, allowing more efforts to be geared towards evaluating and exploring the potential of the new breast-dedicated radiotherapy device in cancer treatment.

While the present disclosure has been shown and described in accordance with practical and preferred embodiments thereof, it is recognized that departures may be made within the spirit and scope of the present disclosure which, therefore, should not be limited except as set forth in the following claims as interpreted under the doctrine of equivalents.

We claim:

1. A system for providing a treatment plan for a stereotactic radiotherapy device comprising:
   a server system communicatively coupled to a backend server of the stereotactic radiotherapy device, wherein the server system is configured to:
      receive from the backend server of the stereotactic radiotherapy device at least one of imaging data of a target area and a first treatment plan generated by the stereotactic radiotherapy device;
      apply a monte-carlo based dose generation module to generate a plurality of doses for locations among the target area; and
      generate a second treatment plan based on the generated plurality of doses;
      wherein generating the second treatment plan comprises:
         generating a fluence map;
         generating a phase space map based on the generated fluence map;
         calculating a dose value for positions within the target area based on the phase space map; and
         compiling the second treatment plan based on the calculated dose values.

2. The system of claim 1, wherein the server system is configured to generate a dose for locations among the target area within a time period of five minutes.

3. The system of claim 1, wherein the server system is configured to generate the second treatment plan within a time period of a week.

4. The system of claim 1, wherein generating the fluence map comprises calculating one or more parameters based on a physical geometry of the stereotactic radiotherapy device.

5. The system of claim 1, wherein the server system is configured to:
   generate a quality assurance report.

6. The system of claim 1, wherein at least a portion of the parameters for the monte-carlo based dose generation module are pre-calculated.

7. The system of claim 1, comprising:
a compact beam scanner configured to obtain beam values and provide the obtained beam values to the dose generation module.

8. A method of providing a treatment plan for a stereotactic radiotherapy device comprising:
receiving from a backend server of the stereotactic radiotherapy device at least one of imaging data of a target area and a first treatment plan generated by the stereotactic radiotherapy device;
applying a monte-carlo based dose generation module stored on a server system to generate a plurality of doses for locations among the target area, wherein the server system is communicatively coupled to the backend server of the stereotactic radiotherapy device; and
generating a second treatment plan based on the generated plurality of doses;
wherein generating the second treatment plan comprises:
generating a fluence map;
generating a phase space map based on the generated fluence map;
calculating a dose value for positions within the target area based on the phase space map; and
compiling the second treatment plan based on the calculated dose values.

9. The method of claim 8, comprising pre-calculating at least a portion of the parameters for the monte-carlo based dose generation module.

10. The method of claim 8, comprising:
receiving data for a physical geometry of the stereotactic radiotherapy device from the backend server of the stereotactic radiotherapy device.

11. The method of claim 8, wherein generating the phase space map comprises using beam values obtained by a compact beam scanner.

12. The method of claim 8, wherein generating the fluence map comprises calculating one or more parameters based on a physical geometry of the stereotactic radiotherapy device.

13. The method of claim 8, comprising:
generating a quality assurance report.

14. A method for verifying a treatment plan of a stereotactic radiotherapy device comprising:
receiving a first treatment plan generated by the stereotactic radiotherapy device;
applying a monte-carlo based dose generation module stored on a server system to generate a plurality of doses for locations among a target area, wherein the server system is communicatively coupled to a backend server of the stereotactic radiotherapy device;
generating a second treatment plan based on the generated plurality of doses;
identifying discrepancies between the received first treatment plan and the generated second treatment plan; and
generating a quality assurance report based on the identified discrepancies;
wherein generating the second treatment plan comprises:
generating a fluence map;
generating a phase space map based on the generated fluence map;
calculating a dose value for positions within the target area based on the phase space map; and
compiling the second treatment plan based on the calculated dose values.

15. The method of claim 14, further comprising receiving imaging data of the target area.

16. The method of claim 14, wherein generating the phase space map comprises using beam values obtained by a compact beam scanner.

17. The method of claim 14, comprising:
integrating the quality assurance report into a graphical user interface for display.

* * * * *